(12) United States Patent
Kassab et al.

(10) Patent No.: US 7,998,153 B2
(45) Date of Patent: Aug. 16, 2011

(54) HOMEOSTATIC TISSUE APPARATUS

(75) Inventors: Ghassan S. Kassab, Zionsville, IN (US);
Jose A. Navia, Sr., Buenos Aires (AR)

(73) Assignee: CVDevices, LLC, Indianapolis, IN (US)

( * ) Notice: Subject to any disclaimer, the term of this patent is extended or adjusted under 35 U.S.C. 154(b) by 425 days.

(21) Appl. No.: 12/304,246

(22) PCT Filed: Jun. 29, 2007

(86) PCT No.: PCT/US2007/015195
§ 371 (c)(1),
(2), (4) Date: Dec. 10, 2008

(87) PCT Pub. No.: WO2008/005370
PCT Pub. Date: Jan. 10, 2008

(65) Prior Publication Data
US 2009/0177211 A1   Jul. 9, 2009

Related U.S. Application Data

(60) Provisional application No. 60/817,419, filed on Jun. 30, 2006, provisional application No. 60/817,420, filed on Jun. 30, 2006.

(51) Int. Cl.
*A61B 17/08* (2006.01)
(52) U.S. Cl. ......................... 606/151; 606/157
(58) Field of Classification Search ............ 606/151, 606/157, 158, 213, 215; 269/86, 95, 147, 269/276; 600/9, 12, 201, 218
See application file for complete search history.

(56) References Cited

U.S. PATENT DOCUMENTS

| | | | |
|---|---|---|---|
| 2,406,567 | A | 8/1946 | Schueneman |
| 3,577,583 | A | 5/1971 | Amann |
| 4,447,238 | A | 5/1984 | Eldridge, Jr. |
| 4,635,636 | A | 1/1987 | Goldstein |
| 5,827,170 | A | 10/1998 | Gebran |
| 6,468,285 | B1 | 10/2002 | Hsu et al. |
| 2006/0079932 | A1 | 4/2006 | Dowling |
| 2006/0100646 | A1 | 5/2006 | Hart et al. |
| 2006/0173453 | A1 | 8/2006 | Gruhl et al. |

OTHER PUBLICATIONS

International Searching Authority, International Search Report, mailed Sep. 17, 2008 (PCT/US2007/015195).
International Searching Authority, Written Opinion of the International Searching Authority, completed Aug. 14, 2008 (PCT/US2007/015195).

*Primary Examiner* — Julian W Woo
(74) *Attorney, Agent, or Firm* — Ice Miller LLP (57) ABSTRACT

A device for supporting a tissue, the device has a shaft having a longitudinal axis and at least two atraumatic clamps coupled to the shaft. Each atraumatic clamp may have at least two oppositely polarized magnets. An atraumatic clamp may also have a mounting structure for the magnets. In at least one embodiment, the atraumatic clamps are mounted along the shaft so that when the shaft is positioned relative to a tissue having a length, the clamps may clamp the tissue so that the length of tissue positioned between the clamps is maintained substantially constant.

26 Claims, 10 Drawing Sheets

HOMEOSTATIC TISSUE APPARATUS

PRIORITY

The present application is a U.S. National Stage Application of International Patent Application Serial No. PCT/US2007/015195, entitled "HOMEOSTATIC TISSUE APPARATUS," filed Jun. 29, 2007, which is related to and claims the benefit of U.S. Provisional Patent Application Ser. No. 60/817,419, entitled "ATRAUMATIC CLAMP," filed Jun 30, 2006, and U.S. Provisional Patent Application Ser. No. 60/817,420, entitled "HOMEOSTATIC TISSUE APPARATUS," filed Jun 30, 2006. The contents of each of these applications are hereby incorporated by reference in their entirety into this disclosure.

BACKGROUND

The disclosure of the present application relates generally to clamps, and more particularly, to homeostatic tissue clamps.

Evidence has shown that the mechanical stresses and strains in the cardiovascular system are under strict regulation, i.e., there exists a homeostatic range of mechanical stresses and strains in the cardiovascular system. These stresses may include homeostatic circumferential stress due to pressure, and axial stress due to axial pre-stretch. A perturbation of the mechanical loading (i.e., change in blood pressure or vessel length) leads to biochemical and biological responses, and these responses may lead to vascular dysfunction including atherosclerosis.

Numerous studies have quantified the degree of longitudinal shortening when a blood vessel is excised from the in situ condition. Computational models have shown that the effect of axial pre-stretch is to increase circumferential and longitudinal stresses. Interestingly, experimental studies have shown that longitudinal retraction or pre-stretch is small in early stages of life and increases with postnatal growth and development as the vessels are stretched by bodily growth. The net effect of these computational and experimental observations indicate that a more similar magnitude of circumferential and longitudinal stresses (homeostasis) may be obtained by pre-stretching the vessel to in vivo levels.

These observations have important implications as a change in blood pressure (hypertension or hypotension) or axial stretch lead to growth and remodeling. In addition to the chronic effects, it is known that removal of vessel and hence axial retraction and circumferential decompression (zero pressure) may cause damage to the endothelium and reduction of nitric oxide (NO). Since NO is atheroprotective, this induces a risk for cell adhesion and thrombosis. In the surgical practice of vessel grafting, the free graft is typically allowed to retract axially and deflate circumferentially which may promote acute vasospasm or thrombosis. Furthermore, the graft is not pre-stretched to the natural in vivo level after implantation which may promote vascular remodeling and stenosis.

Thus, there is a need in the art for a clamping device and a technique of maintaining the natural stress and strain conditions of a tissue that is to be manipulated. The clamping device should be easy to understand and use, universally adoptable, efficient and relatively inexpensive.

SUMMARY

The disclosure of the present application provides devices and methods for securing tissue at two or more locations atraumatically such that the tissue is maintained in its natural stress and strain. According to at least one embodiment presented herein and throughout this disclosure, reference is made to a blood vessel as an example of a tissue that is used with respect to the disclosure of the present application. However, the disclosure of the present application is not limited to blood vessels (arteries and veins) and may be used within any type of tissue, including but not limited to, esophageal tissue, gastric tissue, intestine tissue, and bronchial and lung tissue that could benefit from the use of the disclosure of the present application.

The devices described herein may comprise clamping devices that may "mold" to take shape of a particular tissue to be clamped, contrary to a conventional clamp whereby the tissue takes the shape of the clamp itself. In addition, the clamping pressure of the clamping devices described herein may be pre-set for a particular application, eliminating the need, and risks associated therewith, of having a surgeon attempt to predict the required clamping force.

Using a blood vessel with a device of the disclosure of the present application, the blood vessel can be excised, dissected, removed, attached or anastomosed while maintaining the natural stress and strain forces of the blood vessel. A shaft and multiple attachment pieces are used to maintain the blood vessel in a substantially natural stress and strain configuration while the blood vessel is manipulated.

According to at least one embodiment of a device for supporting a tissue of the disclosure of the present application, the device has a shaft having a longitudinal axis and at least two magnetic clamps mounted along the longitudinal axis of the at least one shaft. In at least one embodiment, the magnetic clamps are atraumatic clamps. In some other embodiments, the magnetic clamps are magnetic collars. The magnetic clamps may also be electromagnetic.

In at least one embodiment, each atraumatic clamp may have at least two oppositely polarized magnets. An atraumatic clamp may also have a mounting structure for the magnets. In at least one embodiment, the atraumatic clamps are mounted along the shaft so that when the shaft is positioned relative to a tissue having a length, the clamps may clamp the tissue so that the length of tissue positioned between the clamps is maintained substantially constant.

In at least one embodiment, a device may also have a power source for providing power to the electromagnets, and an electrical connector coupled to the power source and the electromagnets. Power may be provided by the power source through the electrical connector to electrify at least one of the electromagnets, causing the clamps to clamp a tissue. A device may also have a sensor coupled to the electromagnets, whereby the sensor is operable to detect the level of clamping pressure upon a tissue being clamped. A device may also have a control mechanism coupled to the power source and the sensor, and the control mechanism operable to regulate the power level from the power source used to electrify the electromagnets.

In at least one embodiment, a device has a shaft having a longitudinal axis and at least two electromagnetic collars coupled to the shaft. The electromagnetic collars are mounted along the shaft so that when the shaft is positioned relative to a tissue having a length, the clamps may clamp the tissue so that the length of tissue positioned within the clamps is maintained substantially constant A device may also have a power source for providing power to the electromagnet collars, and an electrical connector coupled to the power source and an electromagnetic collar. Power may be provided by the power source through the electrical connector to electrify at least one of the electromagnetic collars, causing the collars to clamp a tissue. A device may also have a sensor coupled to the electromagnetic collars, and the sensor is operable to detect the level of clamping pressure upon a tissue being clamped. The device may also have control mechanism coupled to the power source and the sensor, and the control mechanism operable to regulate the power level from the power source used to electrify the electromagnetic collars.

According to at least one embodiment of a method for supporting a tissue of the disclosure of the present application, the method has the steps of providing a device for supporting a tissue according to at least one of the aforementioned embodiments, positioning the device relative to a tissue, positioning the clamps around the tissue, and clamping the tissue so that the length of tissue between the clamps is maintained substantially constant.

DETAILED DESCRIPTION

The present disclosure relates to homeostatic tissue clamps and their use for clamping various vessels and tissues. For the purposes of promoting an understanding of the principles of the present disclosure, reference will now be made to the embodiments illustrated in the drawings, and specific language will be used to describe the same. It will nevertheless be understood that no limitation of the scope of the present disclosure is thereby intended.

A basic premise of the present disclosure, and the exemplary embodiments of devices, systems and methods described herein, is to maintain the homeostatic condition of the tissue during surgery to circumvent both the acute as well as the chronic response. In certain exemplary embodiments, a clamp apparatus is presented that assists in fixing the length of the vessel to that of the native environment (in situ), and maintaining intraluminal pressure.

Figure 1A:
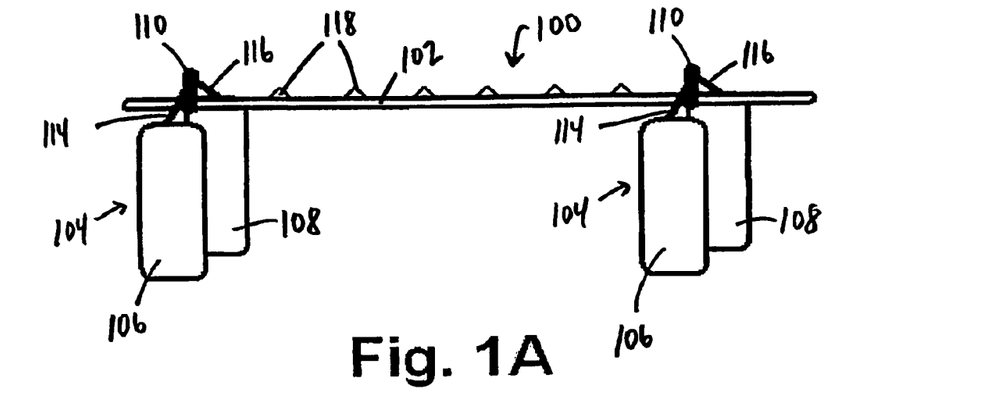
FIG. 1A shows a homeostatic tissue apparatus according to at least one embodiment of the present disclosure having at least two atraumatic clamps.

A homeostatic tissue apparatus according to at least one embodiment of the disclosure of the present application is shown in FIG. 1A. According to at least one embodiment of a homeostatic tissue apparatus 100 of the present disclosure, homeostatic tissue apparatus 100 comprises at least one shaft 102 having a longitudinal axis, and at least two atraumatic clamps 104 mounted along the longitudinal axis of shaft 102. In at least one embodiment, shaft 102 is substantially rigid. According to at least one embodiment, shaft 102 comprises two or more shafts 102. Atraumatic clamps 104 may comprise two atraumatic clamps 104 or may comprise three or more atraumatic clamps 104. In the embodiment shown in FIG. 1A, homeostatic tissue apparatus 100 comprises one shaft 102 having a longitudinal axis and two atraumatic clamps 104 mounted along the longitudinal axis of the shaft 102.

Each atraumatic clamps 104 may comprise first magnet 106 and second magnet 108, whereby first magnet 106 and second magnet 108 are coupled to one another by a mounting structure 110. In at least one embodiment, each atraumatic clamp 104 comprises two magnets. In an additional embodiment, each atraumatic clamp 104 comprises three or more magnets.

First magnet 106 and second magnet 108 comprise magnets with opposing polarities so that the inner surfaces of first magnet 106 and second magnet 108 attract to one another. A magnetic force between first magnet 106 and second magnet 108 attracts first magnet 106 to second magnet 108, noting that the magnetic force may be relatively opposite to a hinge force exerted by the mounting structure 110. First magnet 106 and second magnet 108 may be of any size and/or shape as may be useful with the disclosure of the present application to exert clamping pressure on tissue 112 (shown in FIG. 1B, and is intended to encompass a "vessel" as described herein). Tissue 112 may be positioned substantially in between first magnet 106 and second magnet 108, whereby a magnetic force between first magnet 106 and second magnet 108 bias the magnets toward each other thereby exerting a clamping pressure on tissue 112.

Referring to FIGS. 1B-2B, and according to at least one embodiment of homeostatic tissue apparatus 100, atraumatic clamps 104 are mounted along the longitudinal axis of shaft 102 such that when shaft 102 is positioned relative to tissue 112 having a length, atraumatic clamps 104 may clamp tissue 112 such that the length of tissue 112 positioned between atraumatic clamps 104 is maintained at a substantially constant in situ length.

Figure 7:
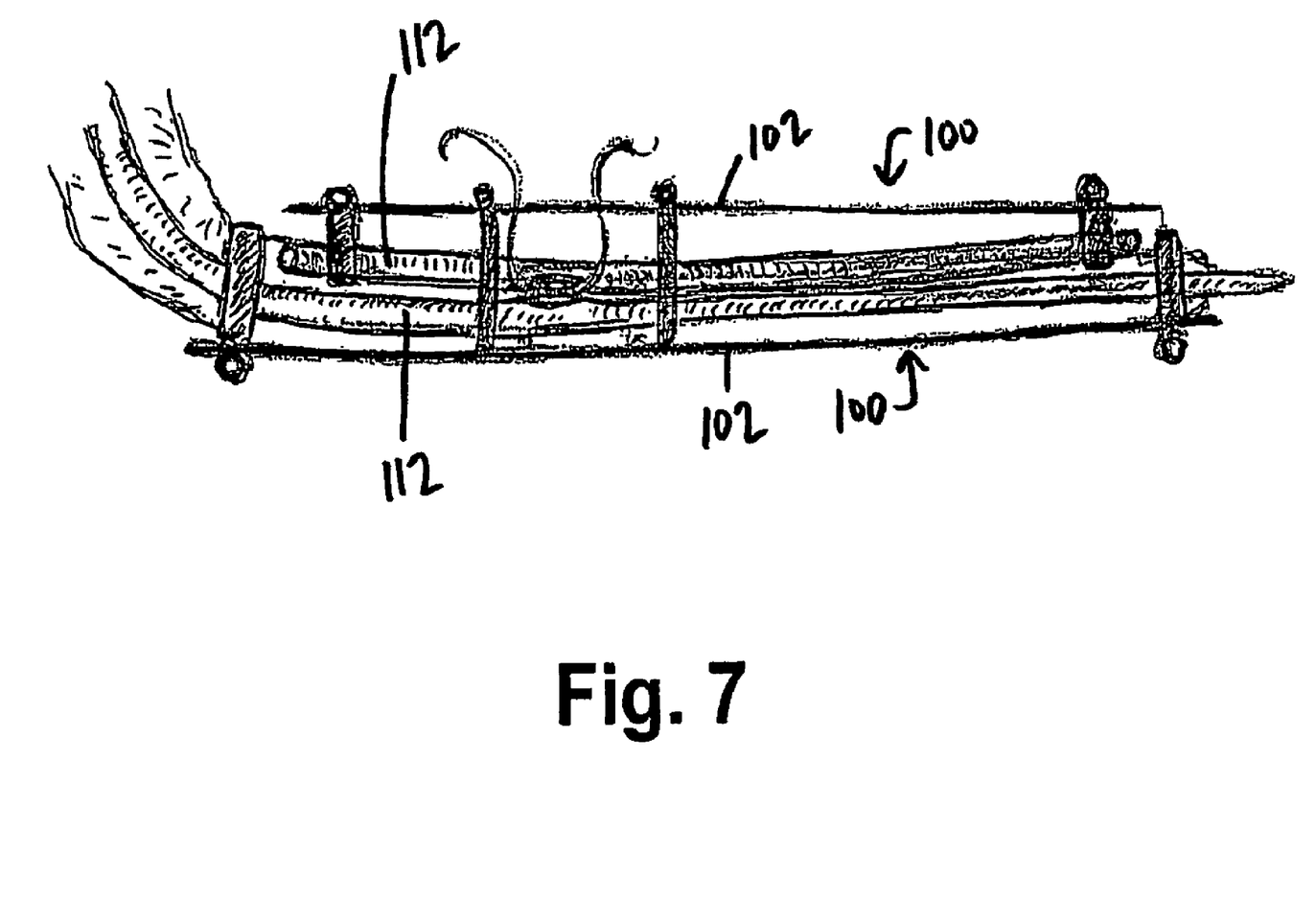
FIG. 7 shows a homeostatic tissue apparatus according to at least one embodiment of the present disclosure utilized for lateral-lateral anastomosis.
Figure 8:
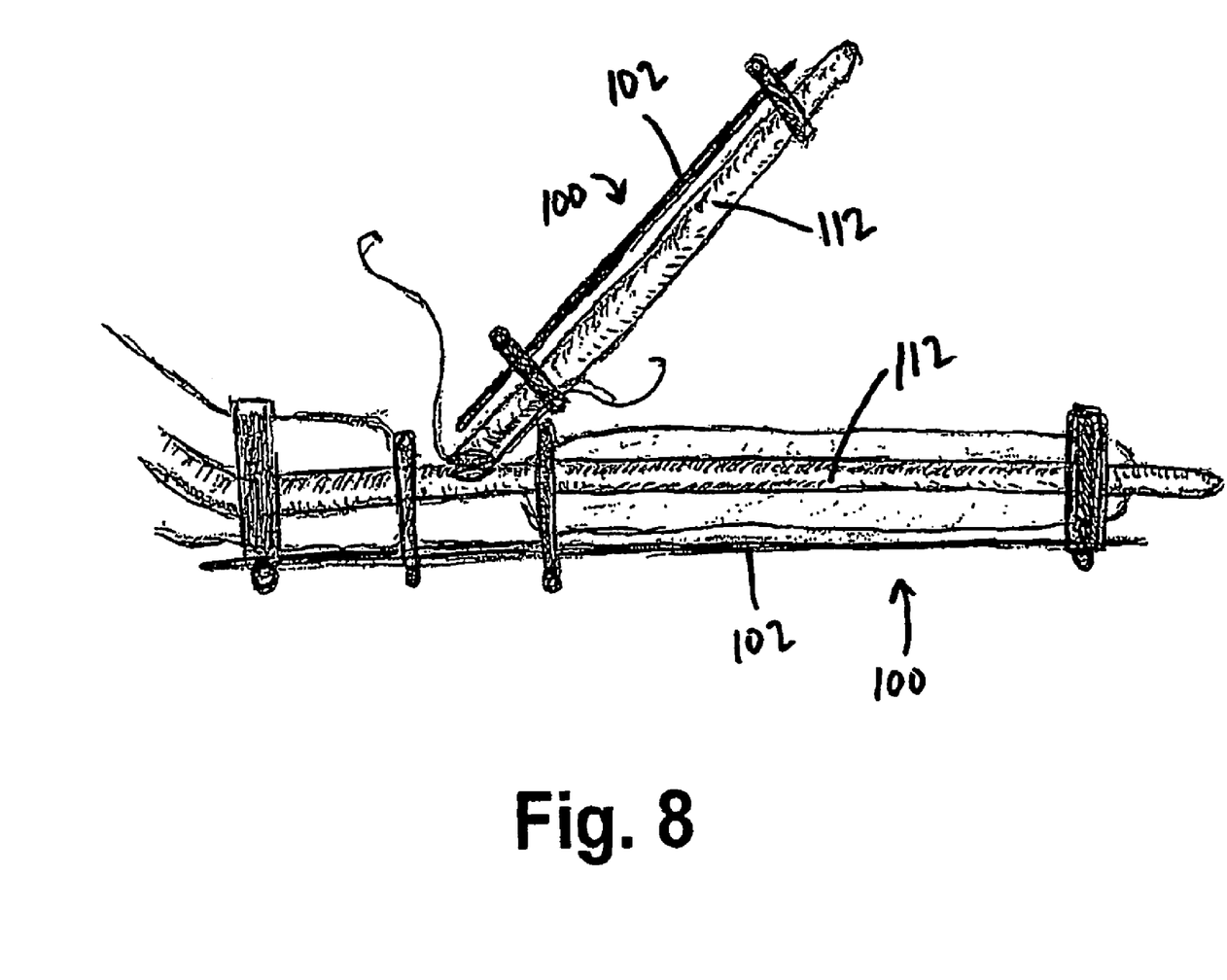
FIG. 8 shows a homeostatic tissue apparatus according to at least one embodiment of the present disclosure utilized for end-to-side anastomosis or T-graft.

In at least one embodiment, tissue 112 may be maintained substantially constant by the use of homeostatic tissue apparatus 100 to allow a user of the device to perform an anastomosis (to surgically connect two or more tissues 112). Homeostatic tissue apparatus 100 can be used to clamp and excise a portion of tissue 112 for its subsequent anastomosis to a second tissue 112, or homeostatic tissue apparatus can be used to clamp tissue 112 to maintain a constant in situ length to allow for the anastomosis of a second tissue 112 along the clamped portion of tissue 112. FIGS. 7 and 8 show examples of tissue 112 anastomosis using homeostatic tissue apparatus 100.

The size and/or shape of first magnet 106 and second magnet 108 may be tailored to a particular clamping application. In addition, a user of atraumatic clamp 104 may be able to "dial-in" a particular clamping force of first magnet 106 and second magnet 108 by adjusting mounting structure 110, by selecting first magnet 106 and/or second magnet 108 of a particular size and/or shape for the intended application, or by regulating power as described herein.

Atraumatic clamps 104 may comprise magnetic material to clamp the vessel symmetrically and gently. The magnetic mechanism of closure or clamp of the vessel minimizes the damage to the vessel. The magnetic clamp force is sufficient to provide the closure force in the presence of physiological pressure. Alternatively, a spring clamp (not shown) may be used to provide adequate force to maintain closure of the vessel without using so much force as to damage the tissue 112.

Additionally, first magnet 106 and/or second magnet 108 may be pliable, i.e., first magnet 106 and/or second magnet 108 may flex and/or contour in respect to a particular tissue 112 positioned substantially in between first magnet 106 and second magnet 108. According to at least one embodiment, first magnet 106 and second magnet 108 of atraumatic clamps 104 comprise pliable magnets. In at least one embodiment, the surface of first magnet 106 and/or second magnet 108 may be coarse, similar to the texture of sandpaper, to minimize slippage of tissue 112 clamped between first magnet 106 and second magnet 108 of atraumatic clamp 104.

As shown in FIG. 1A, mounting structure 110 of atraumatic clamp 104 may comprise a first arm 114 and a second arm 116 each having a distal end. First arm 114 may be hingedly coupled to first magnet 106 at or near its distal end and second arm 116 may be hingedly coupled to second magnet 108 at or near its distal end. Mounting structure 110 may exert a hinge force causing the distal ends of first arm 114 and second arm 116 to extend away from one another. In at least one embodiment, atraumatic clamp 104 comprises one contiguous unitary arm instead of first arm 114 and second arm 116.

According to at least one embodiment, shaft 102 may be threaded through a ring (not shown) present on an atraumatic clamp 104. In an additional embodiment, atraumatic clamp 104 may comprise a clip-like device, to couple atraumatic clamp 104 to shaft 102. The distance between atraumatic clamps 104 along shaft 102 may be altered by sliding atraumatic clamps 104 along shaft 102. In at least one embodiment, shaft 102 may be adjustable so that the shaft may be shortened and/or lengthened as desired by a user (i.e., by the use of two sliding shafts 102).

Shaft 102 may optionally comprise one or more protrusions 118 as shown in FIG. 1. In at least one embodiment of homeostatic tissue apparatus 100, protrusions 118 of shaft 102 may assist atraumatic clamps 104 in maintaining its/their secure position along shaft 102 by its/their coupling at or near one or more protrusions 118, and prevent the sliding of atraumatic clamps 104 on shaft 102.

Figure 1B:
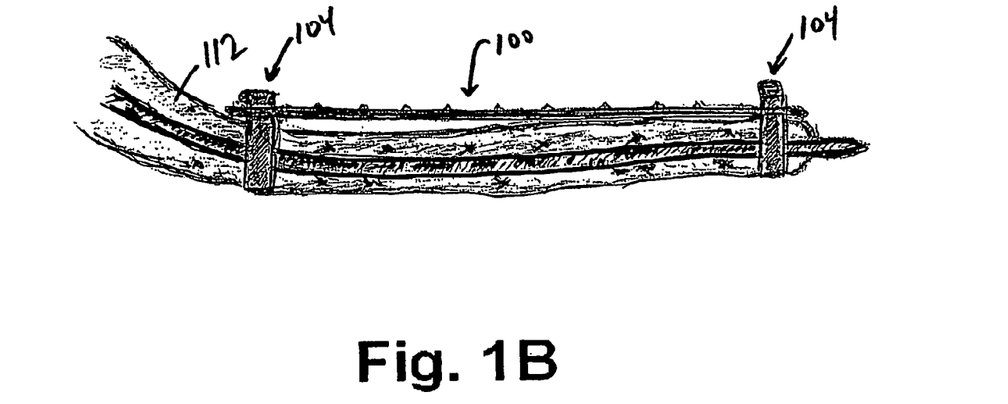
FIG. 1B shows a homeostatic tissue apparatus according to at least one embodiment of the present disclosure engaging a tissue.

FIG. 1B shows an embodiment of homeostatic tissue apparatus 100 of the present disclosure isolating a section of tissue 112. Tissue 112, as shown in FIG. 1B, is a blood vessel. First magnet 106 and second magnet 108 of atraumatic clamp 104 may symmetrically compress tissue 112 with a predetermined force. As shown in FIGS. 1A and 1B, first magnets 106 of atraumatic clamps 104 are positioned on one side of tissue 112, and second magnets 108 of atraumatic clamps 104 are positioned on the opposite side of tissue 112. In this fashion, atraumatic clamps 104 may exert clamping pressure on tissue 112. In this instance, the mode of deformation of tissue 112 does not involve significant shearing of tissue 112 and hence is relatively atraumatic.

Such a minimal force may be predetermined experimentally for different size tissues 112. In a situation where a tissue 112 is a vessel, as is shown in FIG. 1B, atraumatic clamps 104 do not need to completely close the vessel in order to restrict the flow of blood through a vessel as necessary. Near closure of a vessel may cause fluid-solid (blood-vessel) interactions leading to vibrations of a vessel wall. This model of vibration (the small temporal fluctuation of vessel diameter) occurs immediately before full closure of a vessel. These vibrations can be detected by a sensor (e.g., strain gauge) which would then feed back to a control mechanism to control one or more atraumatic clamps 104 of homeostatic tissue apparatus 100 to maintain the force (through the electrical current) at that sensed level of closure. In this example, the majority of flow (99%) would essentially be arrested without completely closing the vessel to avoid trauma of the vessel. Notwithstanding the foregoing, and as may be preferred, atraumatic clamps 104 may be completely closed as to fully restrict the flow of blood through a vessel as desired.

As shown in FIG. 1B, an exemplary embodiment of homeostatic tissue apparatus 100 is placed parallel to the length of the tissue 112. Atraumatic clamps 104 may be used to close off the two ends of the vessel to maintain the mean arterial pressure in the vessel lumen. Once the vessel is excised, shaft 102 will ensure constant length of the vessel.

Figure 2A:
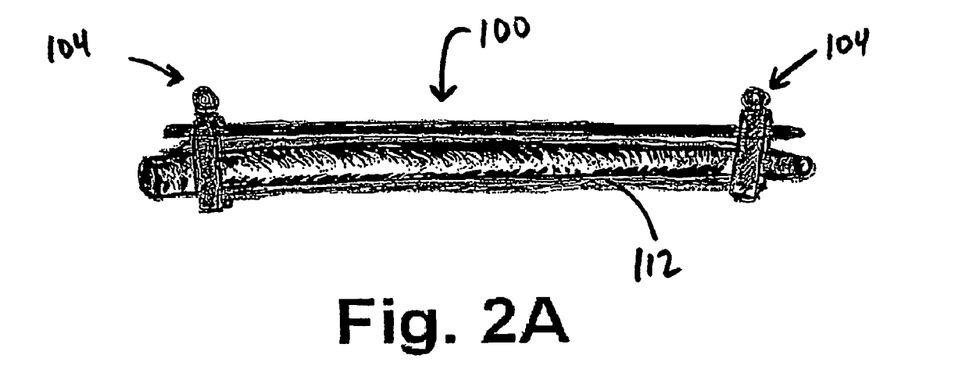
FIG. 2A shows a homeostatic tissue apparatus according to at least one embodiment of the present disclosure engaging a radial artery.
Figure 2B:
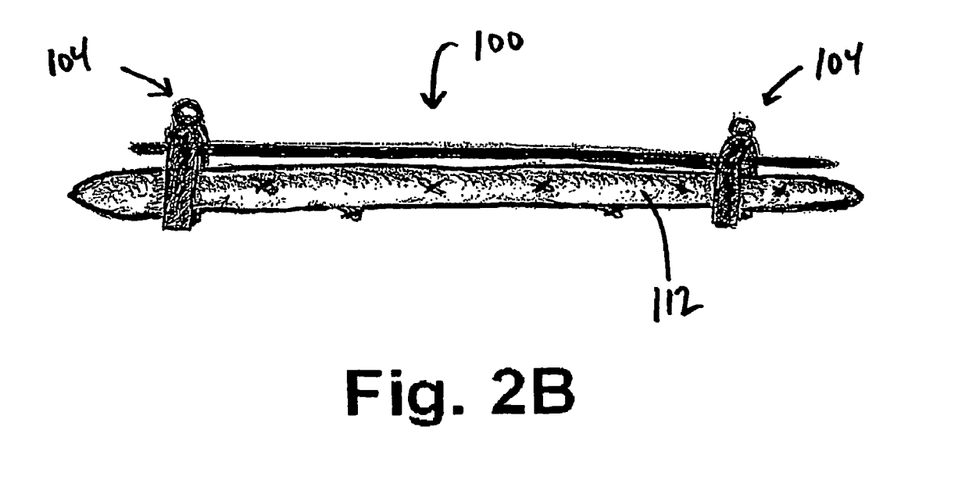
FIG. 2B shows a homeostatic tissue apparatus according to at least one embodiment of the present disclosure engaging a saphenuous vein.

At least one embodiment of homeostatic tissue apparatus 100 of the disclosure of the present application is shown in FIGS. 2A and 2B. In FIG. 2A, an embodiment of homeostatic tissue apparatus 100 is shown securing a radial artery (a tissue 112) using two atraumatic clamps 104. In FIG. 2B, an embodiment of homeostatic tissue apparatus 100 is shown securing a saphenuous vein (a tissue 112) using two atraumatic clamps 104.

Figure 3A:
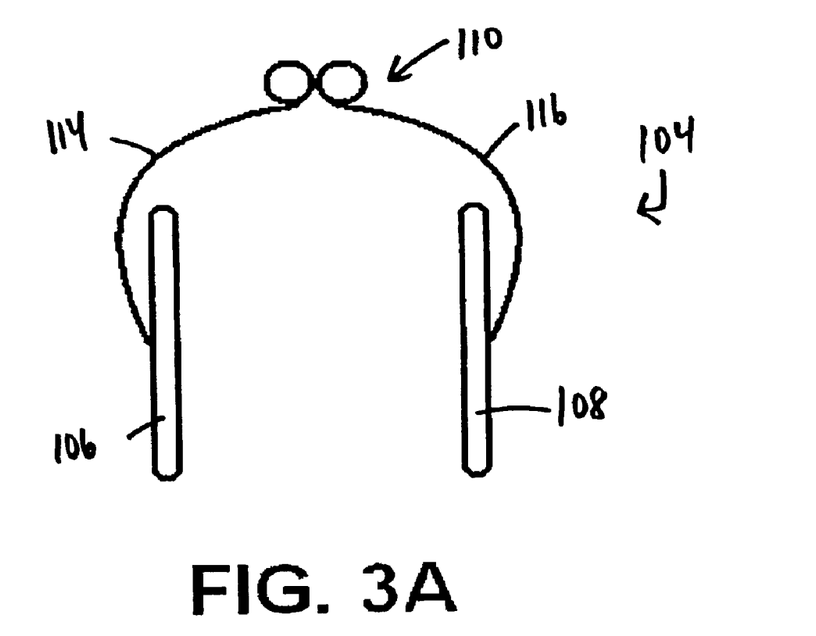
FIG. 3A shows an atraumatic clamp of a homeostatic tissue apparatus according to at least one embodiment of the present disclosure.

An embodiment of atraumatic clamp 104 according to at least one embodiment of the disclosure of the present application is shown in FIG. 3A. Atraumatic clamp 104 comprises first magnet 106 and second magnet 108, whereby first magnet 106 and second magnet 108 are coupled to one another by mounting structure 110. In this embodiment of atraumatic clamp 104, mounting structure 110 comprises first arm 114 and second arm 116. First arm 114 is hingedly coupled to first magnet 106 and second arm 116 may be hingedly coupled to second magnet 108. Mounting structure 110 may exert a hinge force causing the distal ends of first arm 114 and second arm 116 to extend away from one another.

Figure 3B:
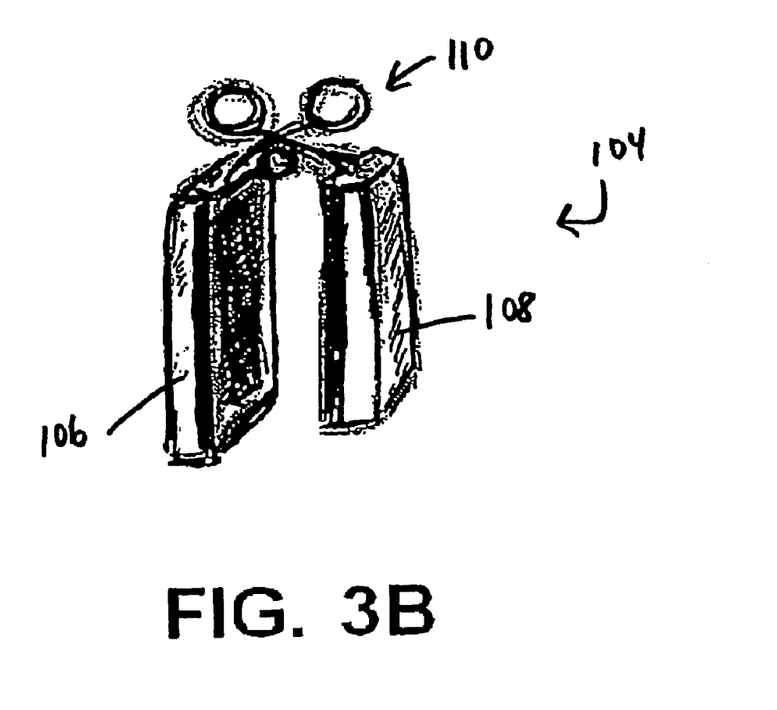
FIG. 3B shows another atraumatic clamp of a homeostatic tissue apparatus according to at least one embodiment of the present disclosure.

An additional embodiment of an atraumatic clamp 104 according to at least one embodiment of the disclosure of the present application is shown in FIG. 3B. In the embodiment shown in FIG. 3B, similar to the embodiment shown in FIG. 3A, atraumatic clamp 104 comprises first magnet 106 and second magnet 108, whereby first magnet 106 and second magnet 108 are coupled to one another by a mounting structure 110. However, in the embodiment of atraumatic clamp 104 shown in FIG. 3B, mounting structure 110 of atraumatic clamp 104 is spring-loaded, and atraumatic clamp 104 may be "opened" by pinching the upper portion of mounting structure 110.

In the case of a diseased or calcified vessel, the deformation of the vessel may be asymmetric, but the asymmetric deformation will avoid excessive compression of at least one vessel particle (not shown), e.g., plaque or calcium, present within the diseased or calcified vessel. According to at least one embodiment of atraumatic clamp 104 of homeostatic tissue apparatus 100, the force is identical on the two poles or plates, but the deformation depends on the elasticity of a vessel. The softer, non-diseased portion of a vessel may deform towards the diseased wall of the vessel. This will minimize the use of excessive force that may cause breakage of at least one vessel particle present within a vessel.

Figure 4A:
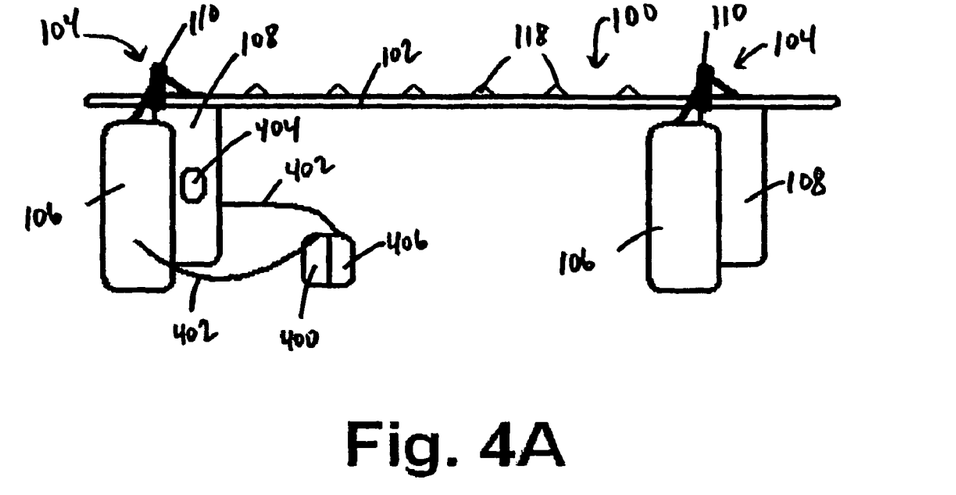
FIG. 4A shows a homeostatic tissue apparatus according to at least one embodiment of the present disclosure operably coupled to a power source.
Figure 4B:
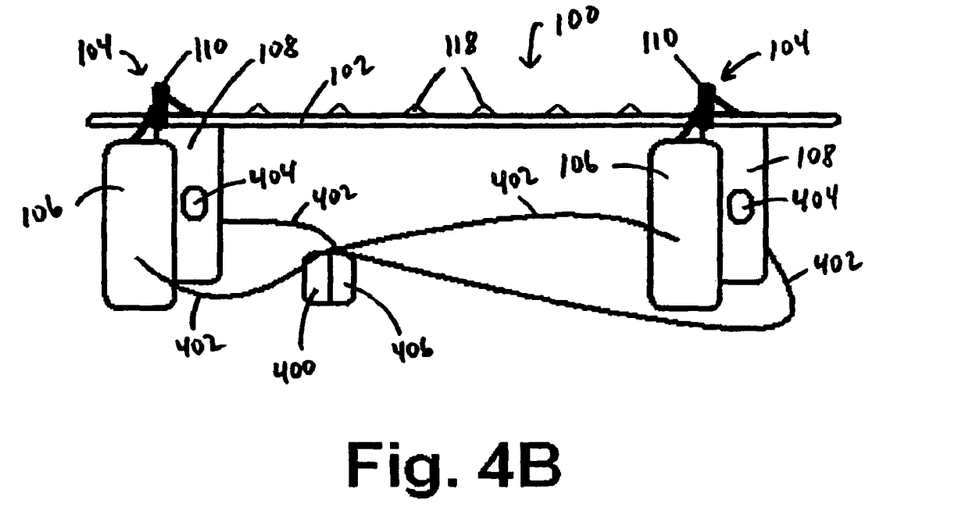
FIG. 4B shows another homeostatic tissue apparatus according to at least one embodiment of the present disclosure operably coupled to a power source.

In at least one embodiment of the present disclosure, homeostatic tissue apparatus 100 may utilize electromagnetic current. Examples of homeostatic tissue apparatuses 100 utilizing electromagnetic current are shown in FIGS. 4A and 4B. Homeostatic tissue apparatus 100 may be "automated", or made "smart", by the use of electromagnetic current flowing from a power source 400 for providing power through at least one electrical connector 402. Electrical connector 402 may be operably coupled between power source 400 and first magnet 106 of atraumatic clamp 104, and another electrical connector 402 may be operably coupled between power source 400 and second magnet 108 of atraumatic clamp 104. In such an embodiment, first magnet 106 and second magnet 108 of atraumatic clamps 104 are electromagnets.

Power source 400 may operate to provide power to at least one magnet (first magnet 106, second magnet 108, etc.) of an atraumatic clamp 104 through electrical connector 402, causing atraumatic clamp 104 to clamp a tissue 112 positioned therebetween.

In such an embodiment, magnetic force is induced through an electric current. Hence, a power driven device may regulate the degree of force required to close a particular tissue 112, like a blood vessel, minimally. Such an embodiment (as discussed herein) may also sense information on the pressure, stress or strain (deformation) of the vessel to regulate the degree of force.

As shown in the embodiment of FIG. 4A, homeostatic tissue apparatus 100 may further comprise at least one sensor 404 operably coupled to at least one magnet (first magnet 106, second magnet 108, etc.) of atraumatic clamp 104. Sensor 404 may operate to detect the level of clamping pressure upon tissue 112 positioned substantially in between at least two of the magnets. FIG. 4A shows an embodiment of homeostatic tissue apparatus 100 comprising one sensor 404 on one atraumatic clamp 104, and FIG. 4B shows an embodiment of homeostatic tissue apparatus 100 comprising one sensor 404 on each atraumatic clamp 104.

As shown in FIGS. 4A and 4B, homeostatic tissue apparatus 100 may also comprise at least one control mechanism 406 operably coupled to the power source 400 and sensor 404, the control mechanism is 406 operable to regulate the level of power provided by power source 400 used to electrify at least one of the magnets (first magnet 106, second magnet 108, etc.) of atraumatic clamp 104. Homeostatic tissue apparatus 100 may comprise both sensor 404 and control mechanism 406 simultaneously.

According to at least one embodiment of homeostatic tissue apparatus 100, control mechanism 406 may be operably coupled to power source 400. In such an embodiment, control mechanism 406 may direct power source 400 to maintain the present level of power when the clamping pressure detected by sensor 404 meets or exceeds a predetermined threshold. FIG. 4A shows an embodiment of homeostatic tissue apparatus 100 comprising control mechanism 406 operably coupled to one atraumatic clamp 104, and FIG. 4B shows an embodiment of homeostatic tissue apparatus 100 comprising control mechanism 406 operably coupled to each atraumatic clamp 104. It can be appreciated that one or more control mechanisms 406 and one or more power sources 400 may be operably coupled to one or more atraumatic clamps 104.

According to at least one embodiment of homeostatic tissue apparatus 100, sensor 404 is operably coupled to control mechanism 406 and is operable to detect a strain in tissue 112. Vessel wall vibrations (as previously discussed) may be a time-varying strain or deformation. Such vibrations of the vessel wall may be detected by sensor 404, which may be an electrical circuit (i.e., Wheatstone bridge), in contact with atraumatic clamp 104. Additional methods to amplify the vibrations to detect the sound waves, similar in principle to microphone amplification, are within the spirit of the present disclosure. In such an embodiment, control mechanism 406 is operable to regulate the level of power provided by power source 400 based upon a level of strain detected in tissue 112 by sensor 404. Such a feedback loop from sensor 404 to control mechanism 406 allows atraumatic clamp 104 to maintain a desired clamping pressure upon tissue 112.

Figure 9:
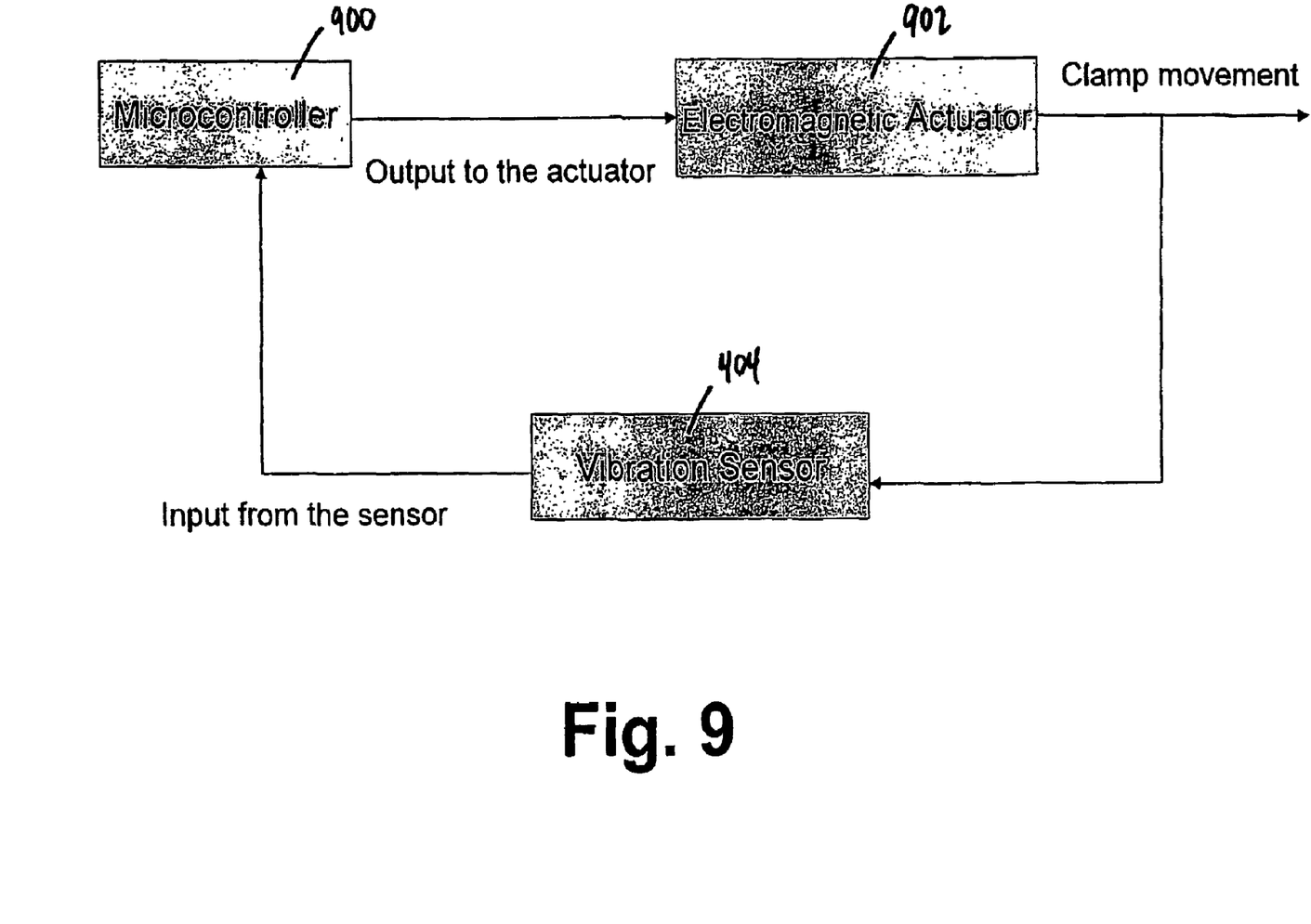
FIG. 9 shows a diagram of the components of a control mechanism according to at least one embodiment of the present disclosure.

In at least one embodiment, a combination of hardware and software to operate control mechanism 406 according to the foregoing is within the scope and spirit of the disclosure of the present application. As shown in FIG. 9, and in at least one embodiment, control mechanism 406 may comprise a microcontroller 900 to provide output to an electromagnetic actuator 902 to control the clamping movement of atraumatic clamp 104 and/or magnetic/electromagnetic collar (as described below). Sensor 404, shown as "Vibration Sensor" in FIG. 9, may provide feedback information to microcontroller 900 based upon information detected by sensor 404.

Figure 10:
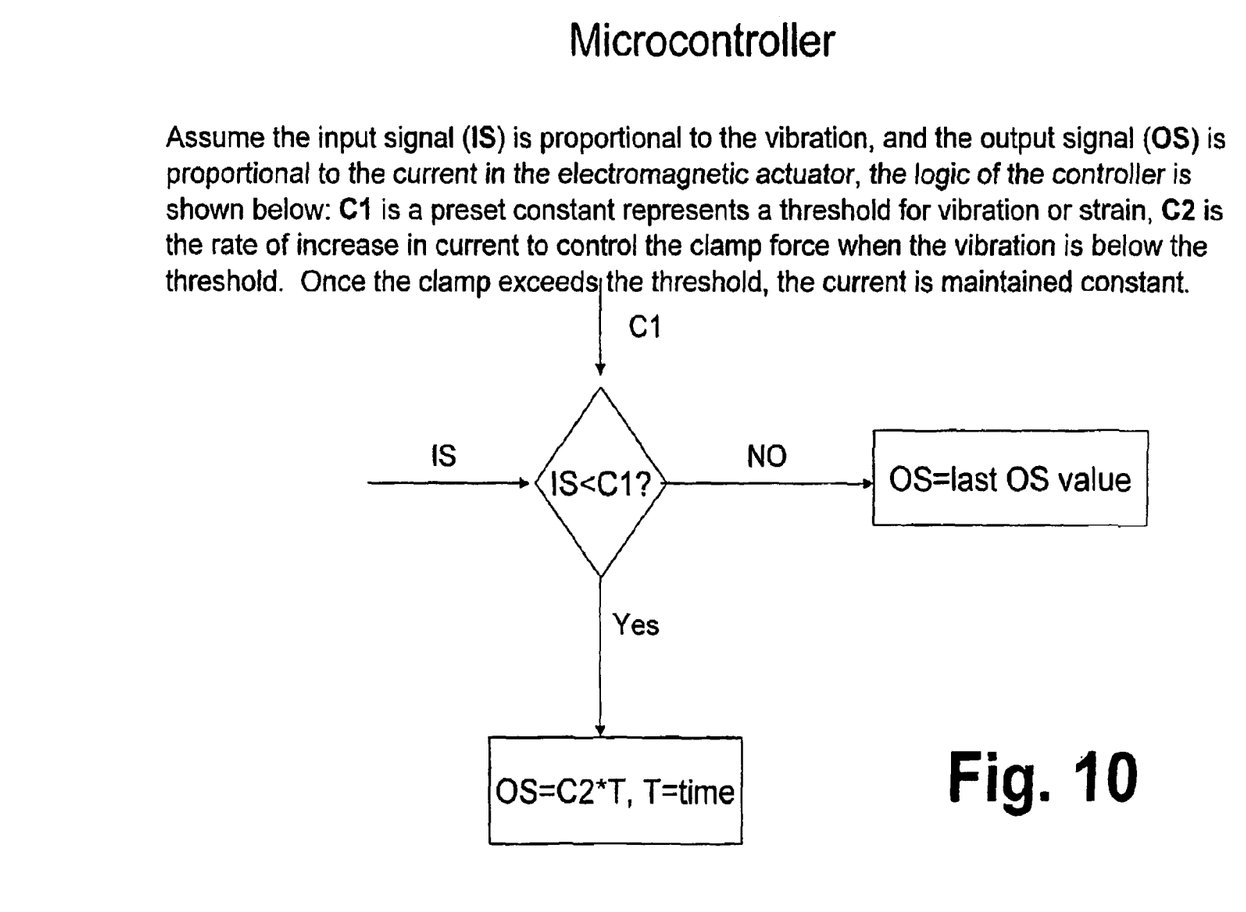
FIG. 10 shows a diagram of the functionality of a microcontroller according to at least one embodiment of the present disclosure.

An example of the functionality of microcontroller 900 is shown in FIG. 10. In this example, an assumption is made that an input signal (IS) is proportional to a vibration (as described above), and an output signal (OS) is proportional to a current in electromagnetic actuator 902. In this example, the logic is shown in the diagram portion of FIG. 10, wherein C1 is a preset constant representing a threshold for vibration or strain, C2 is a rate of increase in current to control atraumatic clamp 104 and/or a magnetic/electromagnetic collar (as described below) force when the vibration is below the preset vibration threshold. Once a clamping device meets or exceeds the threshold, the current/power to the clamping device is maintained constant.

According to at least one embodiment of homeostatic tissue apparatus 100, sensor 404 comprises multiple sensors 404 operably coupled to at least one of the magnets (first magnet 106, second magnet 108, etc.) of atraumatic clamp 104. In such an embodiment, sensors 404 may detect clamping pressure and strain in tissue 112.

Figure 5A:
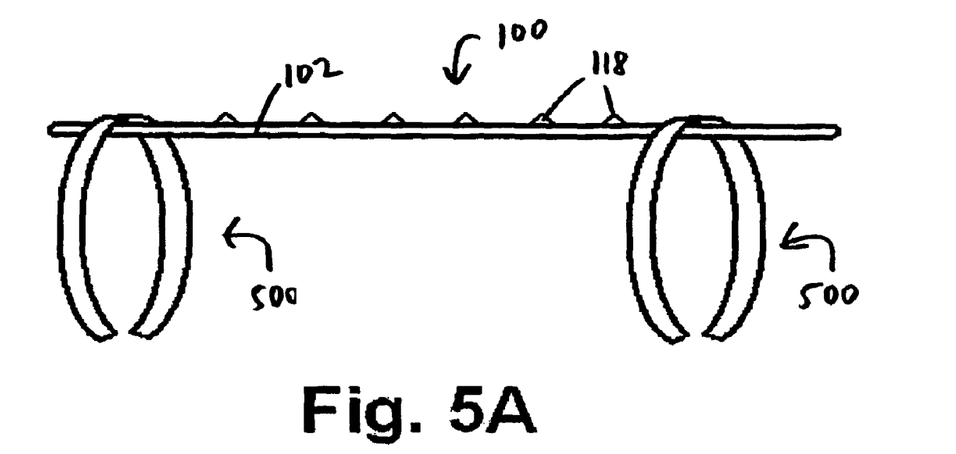
FIG. 5A shows a homeostatic tissue apparatus according to at least one embodiment of the present disclosure having at least two electromagnetic collars.

A homeostatic tissue apparatus 100 according to at least one embodiment of the disclosure of the present application is shown in FIG. 5A. In the embodiment shown in FIG. 5A, homeostatic tissue apparatus 100 comprises at least one shaft 102 having a longitudinal axis, and at least two magnetic collars 500 mounted along the longitudinal axis of shaft 102. In at least one embodiment, magnetic collars 500 are electromagnetic collars. In at least one embodiment, shaft 102 is substantially rigid. According to at least one embodiment, shaft 102 comprises two or more shafts 102. Electromagnetic collars 500 may comprise two electromagnetic collars 500 or may comprise three or more electromagnetic collars 500. In the embodiment shown in FIG. 5A, homeostatic tissue apparatus 100 comprises one shaft 102 having a longitudinal axis and two electromagnetic collars 500 mounted along the longitudinal axis of the shaft 102.

Electromagnetic collar 500 may be pliable, i.e., electromagnetic collar 500 may flex and/or contour in respect to a particular tissue 112 positioned substantially within electromagnetic collar 500. Tissue 112 may be positioned substantially within electromagnetic collar 500, whereby a magnetic force within electromagnetic collar 500 exerts a clamping pressure on tissue 112. Electromagnetic collars 500 may have a gap within electromagnetic collar 500 (as shown in FIGS. 5A-6B) to allow tissue 112 to be positioned substantially within. Electromagnetic collars 500 may be of any size and/or shape as may be useful with the disclosure of the present application to exert clamping pressure on tissue 112. According to at least one embodiment, electromagnetic collars 500 are mounted along the longitudinal axis of shaft 102 such that when shaft 102 is positioned relative to tissue 112 having a length, electromagnetic collars 500 may clamp tissue 112 such that the length of tissue 112 positioned within electromagnetic collars 500 is maintained substantially constant. Electromagnetic collars 500 of homeostatic tissue apparatus 100 may compress tissue 112 with a predetermined force. In this instance, the mode of deformation of tissue 112 does not involve significant shearing of tissue 112 and hence is relatively atraumatic. In at least one embodiment, tissue 112 may be maintained substantially constant by the use of homeostatic tissue apparatus 100 to allow a user of the device to perform an anastomosis.

The size and/or shape of electromagnetic collars 500 may be tailored to a particular clamping application. In addition, a user of electromagnetic collars 500 may be able to "dial-in" a particular clamping force by selecting electromagnetic collars 500 of a particular size and/or shape for the intended application or by regulating power as described herein.

Shaft 102 may optionally comprise one or more protrusions 118 as shown in FIG. 5A. In at least one embodiment of homeostatic tissue apparatus 100, protrusions 118 of shaft 102 may assist electromagnetic collars 500 in maintaining its/their secure position along shaft 102 by its/their coupling at or near one or more protrusions 118, and prevent the sliding of electromagnetic collars 500 on shaft 102.

In a situation wherein a tissue 112 is a vessel, electromagnetic collars 500 do not need to completely close the vessel in order to restrict the flow of blood through a vessel as necessary. As discussed above, near closure of a vessel may cause fluid-solid (blood-vessel) interactions leading to vibrations of a vessel wall. This model of vibration (the small temporal fluctuation of vessel diameter) occurs immediately before full closure of a vessel. These vibrations can be detected by a sensor (e.g., strain gauge) which would then feed back to a control mechanism to control one or more electromagnetic collars 500 of homeostatic tissue apparatus 100 to maintain the force (through the electrical current) at that sensed level of closure. In this example, the majority of flow (99%) would essentially be arrested without completely closing the vessel to avoid trauma of the vessel. However, and as may be preferred regarding an actual excision of tissue 112 as described herein, electromagnetic collars 500 may be completely closed as to fully restrict the flow of blood through a vessel as desired.

Figure 5B:
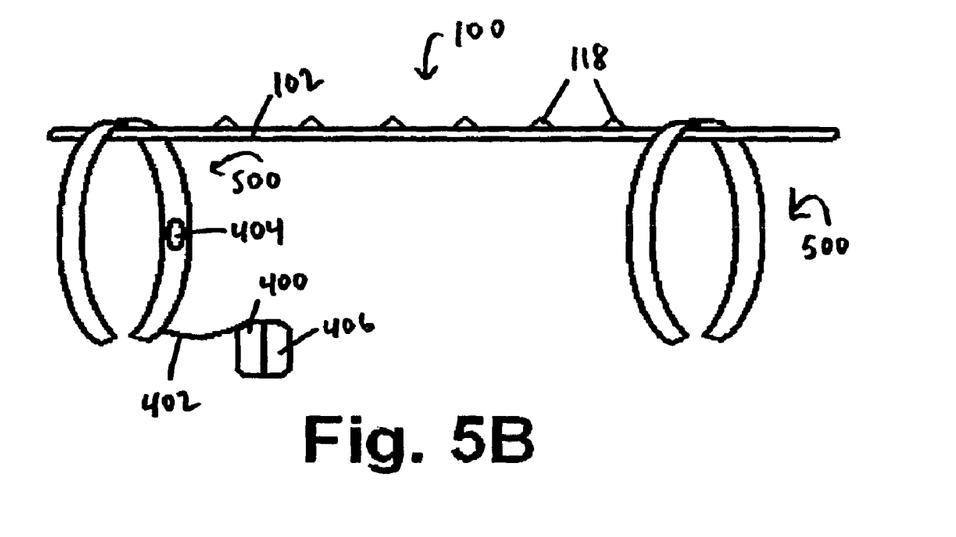
FIG. 5B shows a homeostatic tissue apparatus according to at least one embodiment of the present disclosure having at least two electromagnetic collars and operably coupled to a power source.

As shown in FIG. 5B, homeostatic tissue apparatus 100 may be "automated", or made "smart", by the use of electromagnetic current flowing from power source 400 for providing power through electrical connector 402. Electrical connectors 402 may be operably coupled between power source 400 and electromagnetic collar 500.

Power source 400 may operate to provide power to electromagnetic collars 500 through electrical connector 402, causing electromagnetic collar 500 to clamp a tissue 112 positioned therebetween.

In such an embodiment, magnetic force is induced through an electric current. Hence, a power driven device may regulate the degree of force required to close a particular tissue 112, like a blood vessel, minimally. Such an embodiment (as discussed herein) may also sense information on the pressure, stress or strain (deformation) of the vessel to regulate the degree of force.

According to at least one embodiment of homeostatic tissue apparatus 100, two electrical connectors 402 comprising ferromagnetic bars may be interspersed along the circumference of electromagnetic collar 500. In such an embodiment, the two electrical connectors 302 form the inductors (magnetic dipoles) when the electric current is applied. The magnetic dipoles on the two hemispheres (or halves of the circumference of electromagnetic collar 500) are used to control the force, which is used to compress tissue 112.

As shown in the embodiment of FIG. 5B, homeostatic tissue apparatus 100 may further comprise at least one sensor 404 operably coupled to electromagnetic collar 500. Sensor 404 may operate to detect the level of clamping pressure upon tissue 112 positioned substantially within electromagnetic collar 500. According to at least one embodiment of homeostatic tissue apparatus 100, one may prefer to very the force on tissue 112 locally as to locally deform tissue 112 depending on the circumferential distribution of plaque around the vessel. The concept is not to force a damaged tissue 112, for example a calcified aorta, to take on the shape of a rigid clamp, as that may cause disruption and fracture of the plaque regions within damaged tissue 112. Instead, it may be preferred that the clamp, for example atraumatic clamp 104 and/or electromagnetic collar 500, would take on the shape of tissue 112 being clamped. If the force is controlled at each sensor 404 site, then soft tissue 112 (having no plaque) may deform more than at the location of calcified plaque tissue 112. In this way, homeostatic tissue apparatus 100 may cause little deformation to the calcified regions and deform the soft portions of tissue 112 towards the rigid portion.

As shown in FIG. 5B, homeostatic tissue apparatus 100 may also comprise at least one control mechanism 406 operably coupled to the power source 400 and sensor 404, the control mechanism 406 is operable to regulate the level of power provided by power source 400 used to electrify electromagnetic collar 500. Homeostatic tissue apparatus 100 may comprise both sensor 404 and control mechanism 406 simultaneously.

According to at least one embodiment of homeostatic tissue apparatus 100, including but not limited to the embodiment shown in FIG. 5B, control mechanism 406 may be operably coupled to power source 400. In such an embodiment, control mechanism 406 may direct power source 400 to maintain the present level of power when the clamping pressure detected by sensor 404 meets or exceeds a predetermined threshold.

According to at least one embodiment of homeostatic tissue apparatus 100, sensor 404 is operable to detect a strain in tissue 112. As discussed above, vessel wall vibrations may be a time-varying strain or deformation. Such vibrations of the vessel wall may be detected by sensor 404, which may be an electrical circuit (i.e., Wheatstone bridge), in contact with electromagnetic collar 500. Additional methods to amplify the vibrations to detect the sound waves, similar in principle to microphone amplification, are within the spirit of the present disclosure. In such an embodiment, control mechanism 406 is operable to regulate the level of power provided by power source 400 based upon a level of strain detected in tissue 112 by sensor 404. Such a feedback loop from sensor 404 to control mechanism 406 allows electromagnetic collar 500 to maintain a desired clamping pressure upon tissue 108.

According to at least one embodiment of homeostatic tissue apparatus 100, sensor 404 comprises multiple sensors 404 operably coupled to electromagnetic collar 500. In such an embodiment, sensors 404 may detect clamping pressure and strain in tissue 112.

Figure 6A:
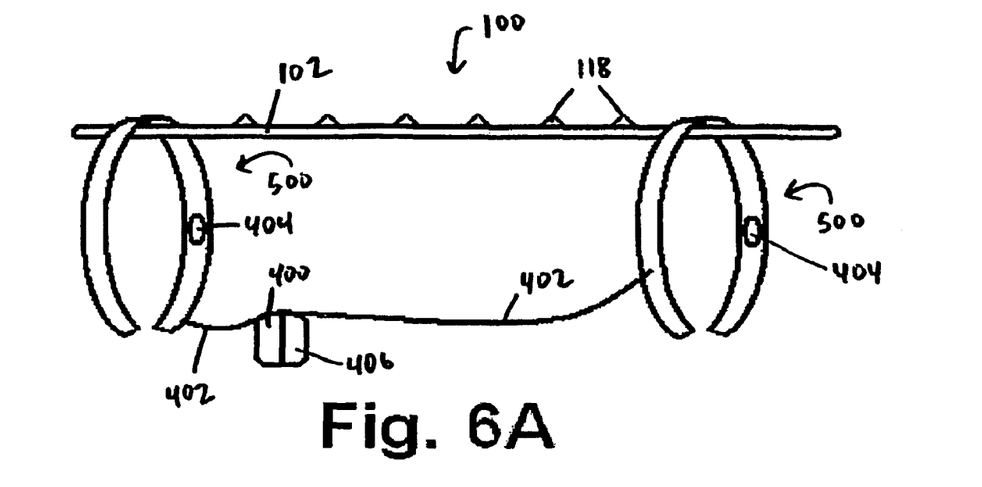
FIG. 6A shows another homeostatic tissue apparatus according to at least one embodiment of the present disclosure having at least two electromagnetic collars and operably coupled to a power source.

At least one embodiment of homeostatic tissue apparatus 100 is shown in FIG. 6A. In this embodiment, homeostatic tissue apparatus 100 comprises one shaft 102 having a longitudinal axis, and two electromagnetic collars 500 mounted along the longitudinal axis of shaft 102. Shaft 102, in this embodiment, comprises one or more protrusions 118 to assist electromagnetic collars 500 in maintaining position along shaft 102. This embodiment further comprises power source 400 providing power through two electrical connectors 402, whereby one electrical connector 402 is operably coupled between power source 400 and one electromagnetic collar 500 and the other electrical connector 402 is operably coupled between power source and the other electromagnetic collar 500. In this embodiment, homeostatic tissue apparatus 100 further comprises two sensors 404, whereby one sensor 404 is operably coupled to one electromagnetic collar 500 and the other sensor 404 is operably coupled to the other electromagnetic collar 500. The operation of power source 400, electrical connectors 402, sensors 404, control mechanisms 406, and electromagnetic collars 500 operate in this embodiment as described herein pertaining to other embodiments.

Figure 6B:
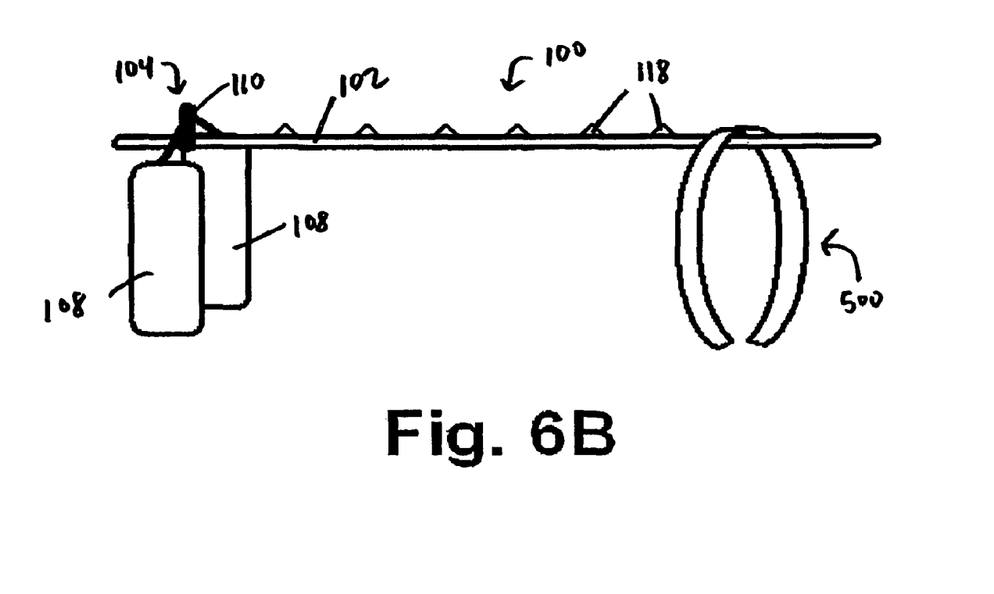
FIG. 6B shows a homeostatic tissue apparatus according to at least one embodiment of the present disclosure having at least one atraumatic clamp and at least one electromagnetic collar.

A homeostatic tissue apparatus 100 according to at least one embodiment of the disclosure of the present application is shown in FIG. 6B. In the embodiment shown in FIG. 6B, homeostatic tissue apparatus 100 comprises at least one shaft 102 having a longitudinal axis, and at least one atraumatic clamp 104 mounted along the longitudinal axis of shaft 102, and at least one electromagnetic collar 500 mounted along the longitudinal axis of shaft 102. In this embodiment, atraumatic clamp 104 may comprise first magnet 106 and second magnet 108, whereby first magnet 106 and second magnet 108 are coupled to one another by a mounting structure 110.

According to at least one embodiment of homeostatic tissue apparatus 100, two electrical connectors 402 comprising ferromagnetic bars may be interspersed along the circumference of electromagnetic collars 500. In such an embodiment, the two electrical connectors 402 form the inductors (magnetic dipoles) when the electric current is applied. The magnetic dipoles on the two hemispheres (or halves of the circumference of the electromagnetic collars 500) are used to control the force, which is used to compress tissue 112.

One or more sensors 404, as discussed herein, may be used to sense pressure or strain on tissue 112 being clamped. A force is increased through an increase in current which is balanced again by sensing pressure, stress or strain (deformation) of tissue 112. The force may be maintained at the point of critical closure, defined as the instance where there is an equilibrium between the applied force and the hemodynamic-elastic force. At the point of critical closure, homeostatic tissue apparatus 100 and/or an homeostatic tissue apparatus 100 control system may sense a "vibration" to indicate the critical closure point. In a calcified or damaged tissue 112, for example a calcified blood vessel, the blood vessel is deformed along the non-diseased portion. If the majority of the vessel circumference is diseased, the force required to compress the vessel may become unacceptably large, and the current may be cut off as predetermined by a preset upper limit on force. This may prevent the crushing of the plaque within tissue 112.

This principle can also be used to decide the area of calcification. A force is generated through the system disclosed herein and the corresponding deformation is recorded. Through variation of force, a force-length or stress-strain relation may be determined using one or more sensors 404 to provide a circumferential profile of compliance or stiffness of tissue 112 which is an indication of health or disease of a particular tissue 112. The data can be represented visually in terms of compliance, elasticity, stiffness, etc. These or similar parameters may be displayed in color circumferentially along a tissue 112 to give a surgeon indications of regions of calcification or plaque. In at least one embodiment, the data on the stiffness modulus (the change in strain over the change in stress) along the vessel circumference can be exported from an electronic spreadsheet, such as, for example, an Excel file, to AutoCAD where the software uses the data coordinates to render a color-map on a monitor.

Permanent magnets of the present disclosure to be selected may be thin, smooth ferromagnetic bars. The saturation hysteresis loop is an important feature for a permanent magnet material. During the process of magnetizing the sample, the magnet is subjected to a field that produces a flux density close to saturation. When the magnetizing field is reduced to zero, the induction drops back to a value. If the magnetizing field is reversed, the magnetic poles of the thin smooth ferromagnetic bars are reversed. According to at least one embodiment of homeostatic tissue apparatus 100, a user may select the specific magnetic field (Tesla) desired for a particular application through appropriate magnetic material. This selection, in conjunction with the design of geometry (dimensions) of a particular magnet (of atraumatic clamp 104 and/or electromagnetic collar 500), a user may determine the appropriate magnetic forces for the vessel or tissue 112 of interest, i.e., a larger force for a larger vessel.

With a wide variation of properties available in permanent magnet materials, the following criteria may be used to specify the optimum material for an apparatus of the present disclosure: (1) Application-Magnetic Field Requirement; (2) Physical or Mechanical-Space Factor, Weight; (3) Stability Requirements; (4) Ductility Requirements; (5) Biocompatibility; and (6) Costs.

It can be appreciated that any number of tissues 112, including but not limited to, veins, arteries, esophageal tissue, gastric tissue, intestine tissue, and bronchial and lung tissue may benefit from the application of an homeostatic tissue apparatus 100 of the present disclosure.

It can also be appreciated that a vessel may not need to be completely closed in order for homeostatic tissue apparatus 100 to function as desired. For example, and depending on the size of a vessel to be clamped, a gap of approximately 100 microns may be small enough to restrict the flow of blood through a vessel to allow for a surgeon to proceed with a surgical procedure.

A homeostatic tissue apparatus 100 or a system comprising a homeostatic tissue apparatus 100 may be utilized for various surgical graft anastomotic procedures. FIG. 7 shows at least one embodiment of homeostatic tissue apparatus 100 of the present disclosure utilized for lateral-lateral anastomosis. As shown in FIG. 7, one homeostatic tissue apparatus 100 has clamped a first tissue 112, and another homeostatic tissue apparatus 100 has clamped a second tissue 112. The two homeostatic tissue apparatuses 100 are then positioned substantially next to one another to allow a surgeon to perform a lateral-lateral anastomosis of the two tissues 112.

FIG. 8 shows at least one embodiment of homeostatic tissue apparatus 100 of the present disclosure utilized for end-to-side anastomosis or T-graft. As shown in FIG. 8, one homeostatic tissue apparatus 100 has clamped a first tissue 112 which has been cut at one end, and another homeostatic tissue apparatus 100 has clamped a second tissue 112. The two homeostatic tissue apparatuses 100 are then positioned so to allow a surgeon to perform an end-to-side anastomosis or T-graft anastomosis of the two tissues 112.

Many other arrangements of at least one embodiment of homeostatic tissue apparatus 100 of the present disclosure can be appreciated within the present framework. For example, tissue 112 may be permitted to rotate like a rotisserie so that a surgeon may have full access to all sides of tissue 112 (360 degrees) for dissection. If desired, tissue 112 may be maintained under homeostatic stress conditions by utilizing at least one embodiment of homeostatic tissue apparatus 100 of the present disclosure until the time of anastomosis. This may have the effect of reducing the duration of the non-physiological conditions of tissue 112.

As described above, at least one embodiment of homeostatic tissue apparatus 100 of the present disclosure does not have to only be used with respect to blood vessels but may also be used to secure any other tissue 112 or tissue 112 structure in place in order to perform a procedure thereon. Such other tissues 112 or tissue 112 systems that may benefit from the use of at least one embodiment of homeostatic tissue apparatus 100 of the present disclosure can be appreciated after consideration of the present disclosure, and are within the scope of the present disclosure.

The foregoing disclosure of the exemplary embodiments of the present application has been presented for purposes of illustration and description and can be further modified within the scope and spirit of this disclosure. It is not intended to be exhaustive or to limit the present disclosure to the precise forms disclosed. This application is therefore intended to cover any variations, uses, or adaptations of a device, system and method of the present application using its general principles. Further, this application is intended to cover such departures from the present disclosure as may come within known or customary practice in the art to which this system of the present application pertains. Many variations and modifications of the embodiments described herein will be apparent to one of ordinary skill in the art in light of the above disclosure. The scope of the present disclosure is to be defined only by the claims appended hereto, and by their equivalents.

Further, in describing representative embodiments of the present disclosure, the specification may have presented the method and/or process of the present disclosure as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present disclosure should not be limited to the performance of their steps in the order written, and one skilled in the art can readily appreciate that the sequences may be varied and still remain within the spirit and scope of the present disclosure.

The invention claimed is:

1. A device for supporting a tissue, the device comprising:
   at least one shaft having a longitudinal axis;
   at least two atraumatic clamps, the at least two atraumatic clamps mounted along the longitudinal axis of the at least one shaft, each of the at least two atraumatic clamps comprising:
     at least two oppositely polarized magnets, wherein the at least two magnets of at least one of the at least two atraumatic clamps are electromagnets; and
     a mounting structure for the at least two magnets;
   a power source for providing power to the electromagnets;
   at least one electrical connector coupled to the power source and further coupled to at least one of the electromagnets of at least one of the at least two atraumatic clamps; and
   at least one sensor operably coupled to at least one of the at least two electromagnets of at least one of the at least two atraumatic clamps, the at least one sensor operable to detect the level of clamping pressure upon a tissue positioned substantially in between at least two of the at least two electromagnets;
   wherein the at least two atraumatic clamps are mounted along the longitudinal axis of the at least one shaft such that when the at least one shaft is positioned relative to a tissue having a length, the at least two atraumatic clamps may clamp the tissue such that the length of the tissue positioned between the at least two atraumatic clamps is maintained substantially constant; and
   whereby power is provided by the power source through the at least one electrical connector to electrify at least one of the electromagnets of at least one of the at least two atraumatic clamps, causing the at least two atraumatic clamps to clamp a tissue positioned therebetween.

2. The device of claim 1, further comprising at least one control mechanism operably coupled to the power source and the at least one sensor, the at least one control mechanism operable to regulate the level of power provided by the power source used to electrify at least one of the at least two electromagnets of at least one of the at least two atraumatic clamps.

3. The device of claim 2, wherein the at least one control mechanism directs the power source to maintain a present level of power when the clamping pressure detected by the at least one sensor meets or exceeds a predetermined threshold.

4. The device of claim 2, wherein the at least one sensor is operable to detect a strain in the tissue.

5. The device of claim 4, wherein the at least one control mechanism is operable to regulate the level of power provided by the power source based upon a level of strain detected in the tissue by the at least one sensor.

6. The device of claim 5, wherein the at least one sensor comprises multiple sensors operably coupled to at least one of the at least two electromagnets of at least one of the at least two atraumatic clamps.

7. The device of claim 6, wherein at least one of the multiple sensors detects clamping pressure and at least one of the multiple sensors detects strain in the tissue.

8. A device for supporting a tissue, the device comprising:
   at least one shaft having a longitudinal axis; and
   at least two atraumatic clamps, the at least two atraumatic clamps mounted along the longitudinal axis of the at least one shaft, each of the at least two atraumatic clamps comprising:
     at least two oppositely polarized electromagnets; and
     a mounting structure for the at least two electromagnets;

a power source for providing power to the at least two electromagnets;
at least one electrical connector coupled to the power source and further coupled to at least one of the at least two electromagnets of at least one of the at least two atraumatic clamps, whereby power is provided by the power source through the at least one electrical connector to electrify at least one of the at least two electromagnets of at least one of the at least two atraumatic clamps, whereby a magnetic force between the electrified at least one electromagnet and at least one of the remaining at least two electromagnets of at least one of the at least two atraumatic clamps is electrically increased;
at least one sensor operably coupled to at least one of the at least two electromagnets of at least one of the at least two atraumatic clamps, the at least one sensor operable to detect the level of clamping pressure upon a tissue positioned substantially in between at least two of the at least two electromagnets; and
at least one control mechanism operably coupled to the power source and the at least one sensor, the at least one control mechanism operable to regulate the level of power provided by the power source used to electrify at least one of the at least two electromagnets of at least one of the at least two atraumatic clamps;
wherein the at least two atraumatic clamps are mounted along the longitudinal axis of the at least one shaft such that when the at least one shaft is positioned relative to a tissue having a length, the at least two atraumatic clamps may clamp the tissue such that the length of the tissue positioned between the at least two atraumatic clamps is maintained substantially constant.

9. A device for supporting a tissue, the device comprising:
at least one shaft having a longitudinal axis;
at least two magnetic collars, the at least two magnetic collars mounted along the longitudinal axis of the at least one shaft, wherein the at least two magnetic collars are electromagnetic collars;
a power source for providing power, the power source electrically coupled to at least one of the at least two electromagnetic collars by at least one electrical connector; and
at least one sensor operably coupled to at least one of the at least two electromagnetic collars, the at least one sensor operable to detect the level of clamping pressure upon a tissue positioned substantially within at least one of the at least two electromagnetic collars;
whereby power is provided by the power source through the at least one electrical connector to electrify at least one of the at least two electromagnetic collars, causing the at least two electromagnetic collars to clamp a tissue positioned therebetween.

10. The device of claim 9, further comprising at least one control mechanism operably coupled to the power source and the at least one sensor, the at least one control mechanism operable to regulate the level of power provided by the power source used to electrify at least one of the at least two electromagnetic collars.

11. The device of claim 10, wherein the at least one control mechanism directs the power source to maintain a present level of power when the clamping pressure detected by the at least one sensor meets or exceeds a predetermined threshold.

12. The device of claim 10, wherein the at least one sensor is operable to detect a strain in the tissue.

13. The device of claim 12, wherein the at least one control mechanism is operable to regulate level of power provided by the power source based upon a level of strain detected in the tissue by the at least one sensor.

14. The device of claim 13, wherein the at least one sensor comprises multiple sensors operably coupled to at least one of the at least two electromagnetic collars.

15. The device of claim 14, wherein at least one of the multiple sensors detects clamping pressure and at least one of the multiple sensors detects strain in the tissue.

16. A device for supporting a tissue, the device comprising:
at least one shaft having a longitudinal axis;
at least two electromagnetic collars, the at least two electromagnetic collars mounted along the longitudinal axis of the at least one shaft, such that when the at least one shaft is positioned relative to a tissue having a length, the at least two electromagnetic collars may clamp the tissue such that the length of the tissue positioned within the at least two electromagnetic collars is maintained substantially constant;
a power source for providing power to the at least two electromagnetic collars, the power source electrically coupled to at least one of the at least two electromagnetic collars by at least one electrical connector, whereby power is provided by the power source through the at least one electrical connector to electrify at least one of the at least two electromagnetic collars, causing the at least two electromagnetic collars to clamp a tissue positioned therebetween;
at least one sensor operably coupled to at least one of the at least two electromagnetic collars, the at least one sensor operable to detect the level of clamping pressure upon a tissue positioned substantially within at least one of the at least two electromagnetic collars; and
at least one control mechanism operably coupled to the power source and the at least one sensor, the at least one control mechanism operable to regulate the level of power provided by the power source used to electrify at least one of the at least two electromagnetic collars.

17. A method for supporting a tissue, the method comprising the steps of:
providing a device for supporting a tissue having a length, the device comprising:
at least one shaft having a longitudinal axis;
at least two atraumatic clamps, the at least two atraumatic clamps mounted along the longitudinal axis of the at least one shaft, each of the at least two atraumatic clamps comprising:
at least two oppositely polarized magnets; and
a mounting structure for the at least two magnets;
positioning the device relative to the tissue;
positioning the at least two magnets of the at least two atraumatic clamps substantially around a tissue;
clamping the tissue with the at least two atraumatic clamps such that the length of the tissue positioned between the at least two magnets of the at least two atraumatic clamps is maintained substantially constant; and
detecting a clamping pressure on the tissue.

18. The method of claim 17, further comprising the step of regulating a magnetic force exerted on the tissue when the clamping pressure meets or exceeds a predetermined threshold.

19. A method for supporting a tissue, the method comprising the steps of
providing a device for supporting a tissue having a length, the device comprising:
at least one shaft having a longitudinal axis;

at least two atraumatic clamps, the at least two atraumatic clamps mounted along the longitudinal axis of the at least one shaft, each of the at least two atraumatic clamps comprising:
at least two oppositely polarized magnets; and
a mounting structure for the at least two magnets;
positioning the device relative to the tissue;
positioning the at least two magnets of the at least two atraumatic clamps substantially around a tissue;
clamping the tissue with the at least two atraumatic clamps such that the length of the tissue positioned between the at least two magnets of the at least two atraumatic clamps is maintained substantially constant; and
detecting a strain within the tissue.

20. The method of claim 19, further comprising the step of regulating a force exerted on the tissue based upon the strain detected within the tissue.

21. A system for supporting a tissue, the system comprising:
a device for supporting a tissue, the device comprising:
at least one shaft having a longitudinal axis; and
at least two atraumatic clamps, the at least two atraumatic clamps mounted along the longitudinal axis of the at least one shaft, each of the at least two atraumatic clamps comprising:
at least two oppositely polarized electromagnets; and
a mounting structure for the at least two electromagnets;
a power source for providing power to the at least two electromagnets;
at least one electrical connector coupled to the power source and further coupled to at least one of the two electromagnets of at least one of the at least two atraumatic clamps, whereby power is provided by the power source through the at least one electrical connector to electrify at least one of the at least two electromagnets of at least one of the at least two atraumatic clamps, whereby a magnetic force between the electrified at least one electromagnet and at least one of the remaining at least two electromagnets of at least one of the at least two atraumatic clamps is electrically increased; and
at least one sensor operably coupled to at least one of the at least two electromagnets of at least one of the at least two atraumatic clamps, the at least one sensor operable to detect the level of clamping pressure upon a tissue positioned substantially in between at least two of the at least two electromagnets.

22. A system for supporting a tissue, the system comprising:
a device for supporting a tissue, the device comprising:
at least one shaft having a longitudinal axis; and
at least two atraumatic clamps, the at least two atraumatic clamps mounted along the longitudinal axis of the at least one shaft, each of the at least two atraumatic clamps comprising:
at least two oppositely polarized electromagnets; and
a mounting structure for the at least two electromagnets;
a power source for providinuower to the at least two electromagnets;
at least one electrical connector coupled to the power source and further coupled to at least one of the two electromagnets of at least one of the at least two atraumatic clamps, whereby power is provided by the power source through the at least one electrical connector to electrify at least one of the at least two electromagnets of at least one of the at least two atraumatic clamps, whereby a magnetic force between the electrified at least one electromagnet and at least one of the remaining at least two electromagnets of at least one of the at least two atraumatic clamps is electrically increased; and
at least one control mechanism operably coupled to the power source and the at least one sensor, the at least one control mechanism operable to regulate the level of power provided by the power source used to electrify at least one of the at least two electromagnets of at least one of the at least two atraumatic clamps.

23. The system of claim 22, wherein the at least one control mechanism operably coupled to the power source directs the power source to maintain a present level of power when the clamping pressure detected by the at least one sensor meets or exceeds a predetermined threshold.

24. A system for supporting a tissue, the system comprising:
a device for supporting a tissue, the device comprising:
at least one shaft having a longitudinal axis; and
at least two electromagnetic collars, the at least two electromagnetic collars mounted along the longitudinal axis of the at least one shaft;
a power source for providing power, the power source electrically coupled to at least one of the at least two electromagnetic collars by at least one electrical connector, whereby power is provided by the power source through the at least one electrical connector to electrify at least one of the at least two electromagnetic collars, causing the at least two electromagnetic collars to clamp a tissue positioned therebetween; and
at least one sensor operably coupled to at least one of the at least two electromagnetic collars, the at least one sensor operable to detect the level of clamping pressure upon a tissue positioned substantially within at least one of the at least two electromagnetic collars.

25. The system of claim 24, further comprising at least one control mechanism operably coupled to the power source and the at least one sensor, the at least one control mechanism operable to regulate the level of power provided by the power source used to electrify the at least two electromagnetic collars.

26. The system of claim 25, wherein the at least one control mechanism operably coupled to the power source directs the power source to maintain a present level of power when the clamping pressure detected by the at least one sensor meets or exceeds a predetermined threshold.

* * * * *